(12) United States Patent
de Vos et al.

(10) Patent No.: US 8,768,457 B2
(45) Date of Patent: *Jul. 1, 2014

(54) RESUSCITATION DEVICE AND METHOD FOR RESUSCITATION

(71) Applicant: NasoPhlex B.V., Zaandijk (NL)

(72) Inventors: Gerrit Johannis de Vos, 's-Heerhendrikskinderen (NL); Zoltán Tomori, Kosice IV (SK)

(73) Assignee: NasoPhlex B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/020,738

(22) Filed: Sep. 6, 2013

(65) Prior Publication Data

US 2014/0025034 A1    Jan. 23, 2014

Related U.S. Application Data

(62) Division of application No. 12/519,346, filed as application No. PCT/NL2006/000599 on Dec. 15, 2006, now Pat. No. 8,532,761.

(51) Int. Cl.
*A61N 1/00* (2006.01)

(52) U.S. Cl.
USPC ..................................... 607/3; 607/6; 607/42

(58) Field of Classification Search
USPC .................................... 607/3, 6, 42
See application file for complete search history.

(56) References Cited

U.S. PATENT DOCUMENTS

| | | |
|---|---|---|
| 4,830,008 A | 5/1989 | Meer |
| 4,969,468 A | 11/1990 | Byers et al. |
| 5,335,657 A | 8/1994 | Terry |
| 5,571,148 A | 11/1996 | Loeb |
| 5,957,956 A | 9/1999 | Kroll |
| 6,368,287 B1 | 4/2002 | Hadas |
| 6,935,335 B1 | 8/2005 | Lehrman |
| 2001/0010010 A1 | 7/2001 | Richmond |
| 2003/0100930 A1 | 5/2003 | Cohen |
| 2003/0139781 A1 | 7/2003 | Bradley |

(Continued)

FOREIGN PATENT DOCUMENTS

| | | |
|---|---|---|
| CA | 2507142 | 10/2006 |
| DE | 29716688 | 11/1997 |

(Continued)

OTHER PUBLICATIONS

Benacka, et al., The sniff-like aspiration reflex evoked by electrical stimulation of the nasopharynx, Respiration Physiology, Dec. 1995, pp. 163-174, vol. 102, No. 2-3.

(Continued)

*Primary Examiner* — Nicole F Lavert
(74) *Attorney, Agent, or Firm* — Meyer IP Law Group

(57) ABSTRACT

A method for providing a resuscitating treatment of a human being, which has the following actions sensing human muscle activity, human breathing activity, human neural activity or human cerebral activity, determining whether the human being is in a state of developing apnoea by a processing unit based on the sensing, provoking an induced aspiration reflex by a resuscitating stimulation of a respiratory area of a human brain stem by providing a stimulus with a stimulation device to a location distant from the respiratory area of the human brain stem upon the processing unit determining the state of developing apnoea, the location being a nasal filter of the human being or a nasopharyngeal area of the human being.

16 Claims, 7 Drawing Sheets

(56) References Cited

U.S. PATENT DOCUMENTS

| | | |
|---|---|---|
| 2003/0199945 A1 | 10/2003 | Ciulla |
| 2004/0176673 A1 | 9/2004 | Wahlstrand |
| 2004/0210261 A1 | 10/2004 | King |
| 2004/0215236 A1 | 10/2004 | Lattner |
| 2004/0243205 A1 | 12/2004 | Keravel |
| 2005/0159790 A1 | 7/2005 | Shalev |
| 2006/0020299 A1 | 1/2006 | Shalev |
| 2006/0064037 A1 | 3/2006 | Shalon |
| 2006/0149319 A1 | 7/2006 | Kuo |
| 2006/0173259 A1 | 8/2006 | Flaherty |
| 2006/0206162 A1 | 9/2006 | Wahlstrand |
| 2006/0217779 A1 | 9/2006 | Ransbury |
| 2007/0084470 A1 | 4/2007 | Sarazen |
| 2007/0088404 A1 | 4/2007 | Wyler |
| 2007/0128420 A1 | 6/2007 | Maghribi |
| 2007/0255379 A1 | 11/2007 | Williams |
| 2007/0255531 A1 | 11/2007 | Drew |

FOREIGN PATENT DOCUMENTS

| | | |
|---|---|---|
| EP | 0404427 | 12/1990 |
| EP | 1790380 | 5/2007 |
| EP | 1825880 | 8/2007 |
| WO | 96/28093 | 9/1996 |
| WO | 00/66215 | 11/2000 |
| WO | 2004/049937 | 6/2004 |
| WO | 2005062829 | 7/2005 |
| WO | 2006/108630 | 10/2006 |
| WO | 2007003019 | 1/2007 |
| WO | 2007146213 | 12/2007 |
| WO | 2007147046 | 12/2007 |
| WO | 2008072948 | 6/2008 |
| WO | 2008080062 | 7/2008 |
| WO | 2008157435 | 12/2008 |

OTHER PUBLICATIONS

Tomori, et al., Mechanisms and clinicophysiological implications of the sniff-and gasp-like aspiration reflex, Repiration Physiology, Oct. 1998, pp. 83-98, vol. 114, No. 1.

Tomori, et al, Hypoxic apnoea induced by N2 inhalation can be reversed by the aspiration reflex in anaesthetized cats, Respiration Medicine, Jan. 1991, pp. 61-65, vol. 85.

Still, et al, Use of acupuncture in the resuscitation of animals, Abstract, U. S. National Library of Medicine, Aug. 1985.

Janssens, et al., Respiratory and cardiac arrest under general anaesthesia: Treatment by acupuncture of the nasal philtrum, Abstract, U. S. National Library of Medicine, Sep. 22, 1979.

Wang, et al., Clinical observation on effect of auricular acupoint pressing in treating sleep apnea syndrome, Abstract, U. S. National Library of Medicine, Oct. 2003.

International Searching Authority, International Search Report and Written Opinion for U. S. International Patent Application No. PCT/NL2006/000599, Aug. 22, 2007, 5 pages.

Miller, Oracl and Pharyngeal Reflexes in the mammalian nervous system: Their diverse range in complexity and the pivotal role of the tongue, Critical Review of Oral Biological Medicine, 2002, pp. 409-425, vol. 13, No. 5.

Loeb, et al., The BION devices: Injectable interfaces with peripheral nerves and muscles, Neurosurgical Focuse, May 2006, pp. 1-9, vol. 20.

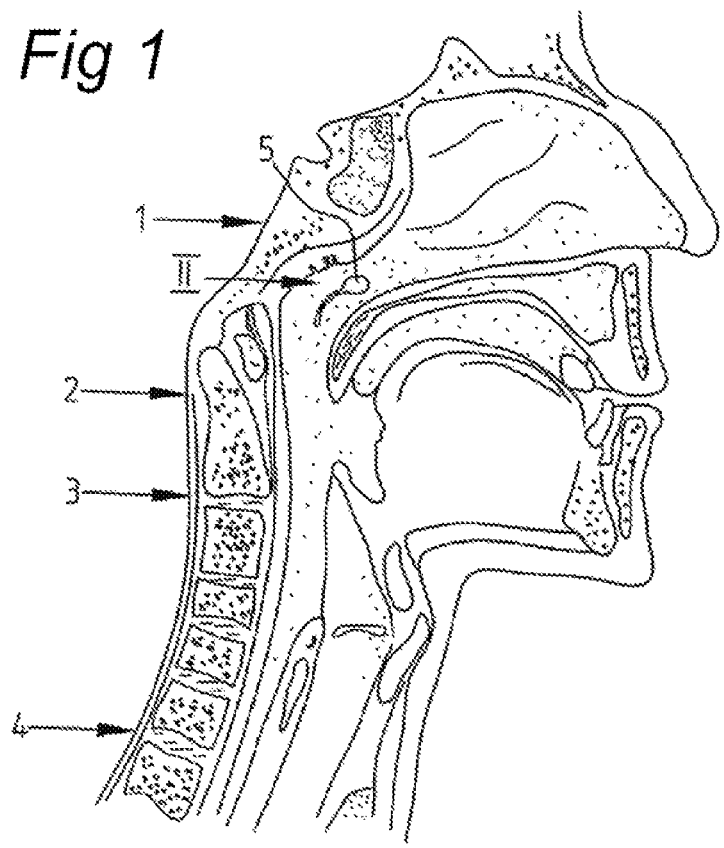
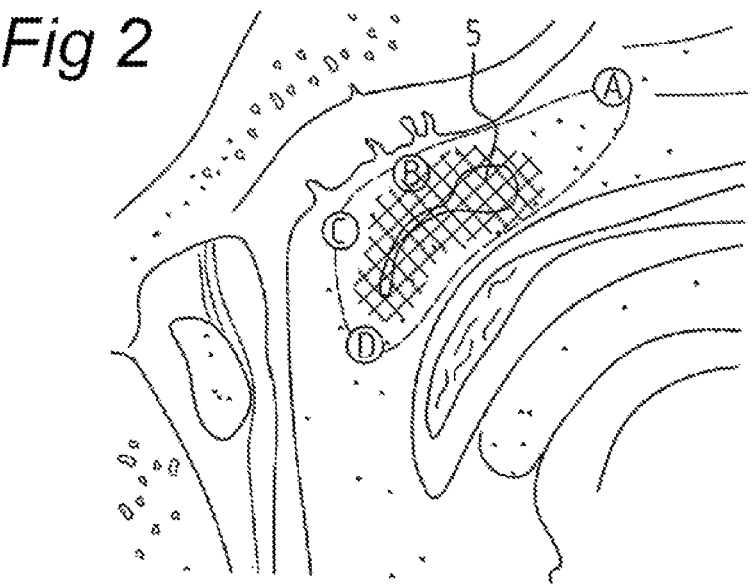

RESUSCITATION DEVICE AND METHOD FOR RESUSCITATION

CLAIM OF PRIORITY

The present application is a division of U.S. patent application Ser. No. 12/519,346, entitled "RESUSCITATION DEVICE AND METHOD FOR RESUSCITATION", by Gerrit Johannis de Vos, et al., filed May 15, 2009, now U.S. Pat. No. 8,532,761, issued on Sep. 10, 2013, which is a 371 of International Patent Application No. PCT/NL2006/000599, by Gerrit Johannis de Vos, et al., filed Dec. 15, 2006, and to U.S. patent application Ser. No. 14/020,739, entitled RESUSCITATION DEVICE AND METHOD FOR RESUSCITATION, by de Vos, et al., filed Sep. 6, 2013, which applications are herein incorporated by reference.

FIELD OF THE INVENTION

According to a first aspect the invention relates to a device for inducing resuscitation in a human subject.

According to a further aspect the invention relates to a method for providing a resuscitating treatment, including but not limited to reversal of life threatening functional disorders, to a human subject in need thereof.

BACKGROUND OF THE INVENTION

The brainstem contains a number of central mechanisms regulating a number of vital physiological functions. Disorders in the regulation of the cardio-pulmonary system can result in a number of pathological conditions some of which may be potentially life threatening.

People suffering from sleep apnoea have cardio-pulmonary disorders manifesting with breathing irregularities and even frequent stops of breathing (apnoea), particularly during sleep, but also during the day. The apnoeic episodes during the day-time are less dangerous, because they can be self managed by conscious actions, apnoeas during the night are more dangerous. Patients can feel very sick in everyday life, due to oxygen deprivation. During episodes of apnoea, blood pressure can collapse and subsequently the heart may stop its function, resulting in inadequate brain perfusion, loss of consciousness and even sudden death. At least 4% of the adult population in developed countries suffers from sleep apnoea.

There are several types of apnoea. One type, central apnoea, involves a dysfunction of the respiratory muscles (including the diaphragm) for lack of command from the respiratory center in the brainstem. This is the type occurring in approximately 10 percent of the cases. Another type, obstructive apnoea, occurs in 80% of cases, when in spite of respiratory movements there is no supply of air to the lungs, due to collapse of the upper airways by strong negative suction pressures. The third type, a mixed apnoea, occurs in the rest of the patients.

It is known, that apnoea can be counteracted by stimulation of the patient in various ways. In infants shaking is usually enough to arouse the baby from sleep and restart the process of automatic breathing and even provoke gasps, which induces resuscitation from asphyxia. Adults suffering from sleep apnoea now sleep with a mask, tightly connected to the facial contours, so a slight over-pressure of air from a device can continuously be applied (Continuous Positive Airway Pressure—CPAP). This keeps the airways open and allows air supply by spontaneous breathing. In any case these patients have to sleep attached to their breathing apparatus, limiting their freedom of movement during sleep. For patients with sleep apnoea travelling means carrying the breathing apparatus with them.

Research in cats has shown that breathing can be stopped by inhalation of anoxic mixtures for over 1 minute, with subsequently a severe drop in blood pressure and heart rate. Mechanical or electrical stimulation of the nasopharynx can induce a sniff- and gasp-like "aspiration reflex" (Tomori and Widdicombe, 1969, Beňački & Tomori, 1995, Tomori et al. 1995, 1998, 2000). Due to resuscitation effects, the blood pressure returns to normal, heart rhythm normalizes, respiration and neuro-behavioral functions return to normal. The anesthetized cat seems to be in good condition, even after as long as three minutes without adequate blood pressure, heart rate and breathing. This experiment can be repeated over 10 times on the same cat, without any noticeable negative consequences.

Provocation of such an aspiration reflex has been indicated as a possible means for interruption of apnoea in cats (Tomori et al., 1991, 1995, Beňački & Tomori, 1995, Jakus et al., 2004). Alternatively, similar resuscitation may be induced by (electro)-acupuncture, (electro)-acupressure or mechanical stimulation of the nasal philter in cats, inducing spasmodic inspiration (Beňački & Tomori, 1997).

However, the current position of the state of the art is that the typical spasmodic inspirations of the aspiration reflex provoked from the nasopharynx and oropharynx in cats are not notable in humans and in this latter species are superimposed by a strong vomiting reflex (Beňački, 2004). Other researchers found reactions different from the aspiration reflex in humans in response to stimulation of the upper airways with high-frequency oscillating air pressure (Henke & Sullivan, 1992).

Therefore, there is no suggestion in the prior art to provide resuscitating stimulation of the brainstem with an induced aspiration reflex in a human in order to obtain resuscitating physiological effects. Also no suitable devices designed for treating apnoea and related cardio-respiratory syndromes in humans via activation of the respiratory center of the brainstem followed by an induced aspiration reflex are available on the market.

The inventors of the present invention have now surprisingly discovered that resuscitating stimulation of the respiratory area of the brainstem in humans following an induced aspiration reflex does provide beneficial effects to subjects suffering from or having a predisposition for several cardio-respiratory or neurobehavioral disorders of functional character, including apnoea, such as central apnoea and/or obstructive apnoea. This without any noticeable negative effects.

It is believed that the "aspiration reflex", via strong activation of the inspiratory center, causes the controlling functions of the brainstem to be reset, similar to activation of brainstem centers during autoresuscitation induced by gasping. In rapid and strong inspiratory effort during a gasp or a provoked aspiration reflex, activation of the inspiratory center in the brainstem resets the failing centers of other vital functions, including the centers controlling cardiac activity, blood pressure, as well as various neuropsychic and somato-motor functions. Without wishing to be bound by any theory it is believed that in relation to the following 5 groups of conditions the invention works via the indicated mechanisms.

1) In patients with apnoea and hypopnoea caused by transient inactivity of the inspiratory neurons in the brainstem, induction of the aspiration reflex can reverse the apnoea or hypopnoea and restore spontaneous breathing. In patients with obstructive apnoea, the stimulation of the inspiratory center in the brainstem may reverse the closure of the airways and restore normal breathing.

2) In patients with Transient Ischemic Attack (TIA), syncope, hypotension, migraine and hemorrhagic shock the aspiration reflex activates, via the respiratory centre, the brainstem vasomotor center to evoke vasoconstriction, resulting in increase of blood pressure and consequently increased brain perfusion, interrupting, terminating or at least alleviating the pathological condition.

3) Bronchospasm, laryngospasm, hiccup, epileptic seizures, and tremor in Parkinson's disease may be inhibited by impulses from the inspiratory center via the reticular formation, transmitted through interneurons providing inhibitory influence to the relevant control centers in the brainstem and elsewhere.

4) In alternating hemiplegia, sleep paralysis and absence type epilepsy: stimulation via the inspiratory center and interneurons activates the descending part of the reticular formation, which activates motoneurons, terminating, or at least alleviating the attack.

5) In comatose states, depression, insomnia, Alzheimers disease, anorexia nervosa, bulimia, and autism, stimulation via the inspiratory center and interneurons influences the ascending part of the reticular formation. This inhibits or provides relief in depression, bulimia, anorexia nervosa and increases concentration and other cognitive functions. This improves some comatose states, may inhibit the development of Alzheimer's disease and autism and has a positive influence on insomnia and psychiatric disorders.

The benefits of resuscitation by stimulation of the respiratory center of the brainstem with an induced aspiration reflex for these conditions was not identified before in the prior art.

The present invention aims at providing a solution to the above shortcoming of the prior art. For this the invention in one aspect provides a resuscitation device comprising:

a number of sensor means for detecting a number of parameter values;

at least one memory means for storing a number of predetermined functions and optionally a number of detected parameter values;

at least one processing means connected with the sensor means and the memory means for processing the number of detected parameter values in said predetermined function.

a number of response means connected with the processing means for providing a response as a function of the number of processed parameter values.

The device according to the invention is characterized in that the number of response means comprises a number of stimulation means designed to provide resuscitating stimulation of the respiratory area of the brain stem. Resuscitating stimulation of the inspiratory neurons of the brain stem should be understood to mean stimulation of the human body such that the aspiration reflex or its alternatives are induced, which will influence various brainstem centers. Through such stimulation other parts of the brain relevant for the conditions treatable with the device are influenced. The aspiration reflex and its alternatives have as a common feature strong and short inspiratory efforts comparable to that occurring before or during one or more of gasp, sniff, sigh or augmented breath. Preferably stimulation of the inspiratory area of the brain stem is from a location distant from said brainstem.

The device according to the invention is suitable for inducing autoresuscitation in a subject in need thereof. The term autoresuscitation should be understood to comprise resuscitation by activation of natural compensatory mechanisms of the human organism via inducing a sniff- and gasp-like aspiration reflex, or its alternative forms in various species, similar to that provided by means of spontaneous gasping autoresuscitation observed in non-human animals and human infants (Sridhar et al., 2003; Xie et al., 2004). When referring to induction of autoresuscitation in this specification the term resuscitation may be used. Subjects that may benefit from induction of autoresuscitation are subjects suffering from and/or having a predisposition for functional disorders, such as hyper and hypo-function of the: a) respiratory system, b) cardiovascular system, c) neurobehavioral changes and d) psychiatric disorders, as discussed above. These include one or more of apnoea, transient ischemic attacks (TIA), bronchospasm also in asthmatics, laryngospasm, hiccup, tremor associated with Parkinson's disease, epileptic seizure, absence type epilepsy, migraine, hypotension, syncope, haemorhagic shock (loss of blood), alternating hemiplegia, Alzheimers disease, depression, anorexia nervosa, bulimia, autism, psychiatric disorders, sleep paralysis, insomnia, comatose states.

The sensor means may be any suitable means for detecting a number of parameter values. In the present specification a number shall mean one or more unless explicitly stated otherwise. The sensor means may provide an electric output representing determined parameter values in response to the determined parameter values. The determined parameter values are values of a parameter as measured/determined by the sensor within a certain time frame. The parameter may be any parameter on the basis of which it may be determined whether a subject is in need of induction of autoresuscitation.

Parameters suitable for determining whether a subject is in need of resuscitation include but are not limited to parameters corresponding to muscle activity, parameters corresponding to breathing, or parameters corresponding to cerebral activity, such as electrical activity of neural cells including brain cells, or electrical activity recorded from the pharynx.

Parameters corresponding to muscle activity include but are not limited to movement and electrical activity of muscles. Movement of muscles may be detected by any sensor means suitable for detecting movement, such as a number of accelerometers. Electrical activity of muscles may be detected by use of any suitable means known in the art such as means conventionally used for detecting an electromyogram (EMG), including an electrocardiogram (ECG), electroneurogram (ENG), actogram indicating contraction, etc.

Parameters corresponding to breathing, include but are not limited to parameters corresponding to activity of muscles involved in breathing activity such as, the diaphragm, the intercostal muscles, musculus pectoralis, abdominal muscles, muscles of the upper and lower airways and other muscles involved. The parameters corresponding to muscle activity as discussed above are suitable. In an alternative embodiment of the device according to the invention the parameter corresponding to breathing activity may comprise gas flow in the airways and/or in the vicinity of the inlets/outlets of the subject's airways. It must be understood that the inlets/outlets of the subject's airways comprise normally the nostrils and/or mouth or a tracheal tube in some patients. The skilled person will be familiar with suitable means for determining gas flow, e.g. by a pneumotachograph or thermometer, such as a thermistor, Pt100, Pt1000 and other.

In a further alternative embodiment of the device the parameters corresponding to breathing activity may comprise sound. During breathing sounds are created. Respiratory sounds include but are not limited to snoring, inspiratory and expiratory stridor, groaning, etc. These sounds may be used to detect the breathing activity. Suitable sensor means for detecting sounds are microphones, a membrane connected to a coil/magnet system or any other device comprising a membrane with the possibility to register movement or displacement of this membrane.

Parameters corresponding to neural activity include but are not limited to electrical activity of nerve cells, or fibers (electroneurogram—ENG), including brain cells. Electrical activity of nerve cells may be detected by use of any suitable means known in the art such as means conventionally used for detecting an electroencephalogram (EEG), such as measuring potential differences between different positions on the scalp. Another possibility is measuring changes in the magnetic field resulting from the electrical activity, by recording currents through coils placed in these magnetic fields. In general various positions on the top of the skull are used, but for this application positions beneath the basis of the brain, in the oro-nasal cavity may also be used. EEG activity may also be recorded from the pharynx, more specific from the nasopharynx.

A further method is by measuring activity of the muscles providing eye ball movements (electrooculography—EOG), generally used e.g. for determination of rapid eye movements (REM) sleep.

The device according to the invention further comprises at least one memory means for storing a predetermined function and optionally a number of detected parameter values. The memory means may be any suitable memory means for storing a predetermined function such as a computer readable memory. The predetermined function may be a mathematical function or correlation. Suitable functions may be functions that are suitable for determining whether a determined parameter value is equal to, greater than or smaller than a predetermined threshold value. Based on his knowledge the skilled person will be able to determine suitable functions on the basis of which a response is required as a function of the determined parameter values. E.g. the function may relate the absence of certain parameter values below a certain threshold value to a certain time frame. Such a function may be determined to detect the absence of breathing during a certain time period e.g. 5 seconds and longer or 10 seconds and longer.

In a preferred embodiment of the invention the number of memory means is suitable for storing a number of detected parameter values. The skilled person will be able to select suitable memory means for storing detected parameter values. Computer readable memory means may be suitable. The device according to the invention further comprises at least one processing means connected with the sensor means and the memory means for processing the number of detected parameter values in said predetermined function. The processing means may be a microprocessor. In the processing means detected parameter values detected by the sensor means are processed in the predetermined function. For this the detected parameter values are loaded into the processing means either directly from the sensor means or alternatively from the memory means into which the detected parameter values were previously loaded. The predetermined function is loaded in the processing means from the memory means or in an alternative embodiment the predetermined function may be embedded in said processing means. In the latter embodiment at least one memory means may be (partially) integrated in the processing means. The device further comprises a number of response means connected with the processing means for providing a response as a function of the number of processed parameter values. The number of response means comprises a number of stimulation means designed to provide resuscitating stimulation in order to stimulate and/or reactivate the inspiratory center of the brainstem. The inspiratory center of the brainstem may be stimulated directly using microelectrodes inserted into the lateral tegmental field of medulla to provoke sniff-, gasp- and hiccough-like spasmodic inspiration in non-human animals (Batsel and Lines, 1973, St John et al., 1984, 1996, Arita H, et al., 1994). Alternatively it may be activated indirectly by stimulation of a location distant from the brain stem. The primary preferred stimulation goes from the upper airways, preferably the pharynx, to the inspiratory center in the brainstem. In the brainstem there are other controlling centers, such as the vasomotor center and the neurons controlling cardiac activity, which will as a result also be influenced secondarily to the stimulation of the inspiratory center. Furthermore, the inspiratory center is connected by interneurons to the reticular formation (RF). The descending part of the RF connects to the peripheral nervous system, such as various motor and sensory neurons; the ascending part connects to higher centers controlling e.g. sensation, perception and cognitive functions.

Stimulation of certain locations distant from the brain stem results in induction of resuscitation because in certain locations of the mammalian body afferent nerves connected to the inspiratory center of the brainstem are present. Stimulation of such afferent nerves or their receptive zones results in activation of the inspiratory center of the brainstem and through this in influencing of the other centers in the brainstem and other parts of the brain such that resuscitation and/or autoresuscitation may be induced.

Preferably the resuscitating stimulation of the inspiratory center of the brain stem is at a location distant from said inspiratory center. Examples of such areas include the upper airways, preferably the pharynx, acupuncture point GV26 on the nasal philter and acupuncture points on the auricle of the ear. Stimulation of the nasopharynx, more preferably the part of the nasopharynx in the proximity of the tubae auditivae, is preferred as it provides the strongest resuscitation effect with induction of the aspiration reflex.

The stimulation means may be electrical stimulation means. Electrical stimulation means may include a power source and/or a wave generator. In combination with an adequate power source, a wave generator can produce block waves, sinus waves and spikes of different length, frequency and amplitude.

The electrical stimulation means may further include electrodes for delivering the electrical stimulation to the body of the subject. Electrodes may be mono-polar or multipolar, including bipolar electrodes and may be placed on the surface of the body or anchored in various tissues of the subject's body. For stimulation of acupuncture point GV26 on the nasal philter and acupuncture points on the auricle of the ear, the electrodes may be placed on the skin. Alternatively electrodes may have the form of needles at least partially penetrating the subject's skin. For stimulation of the pharynx the electrode may be anchored in the subject's pharynx.

In a preferred embodiment a plurality of stimulatory electrodes and a number of collecting electrodes is used. By using a plurality of stimulatory electrodes more complex stimulation currents can be provided. This also provides the possibility of precise definition of the area to be stimulated. If a plurality of electrodes is used it is preferred that there is some distance between said electrodes. Due to this distance the electrical current will travel over that distance through the subject's body. This will enhance the stimulatory effect. In cardiac pacemakers a spike stimulation is used (e.g. 1.2 V, 20 millisecond). Variations in the amplitude and duration of the spike, i.e. the amount of energy can be made, apart from trains of spikes over an extended period of time (seconds) (Beňački and Tomori, 1995). Sinus waves of various frequencies and duration, block waves, spikes, spike trains and any combination of these can be used. It is preferred to not just transfer energy, but to stimulate the targeted response centers more complexly to elicit the desired physiological response.

The electro-stimulation lead is anchored to the selected area of the subject's body by means of an anchoring means. Any suitable anchoring means as known in the art for anchoring an electro-stimulation lead to a mammalian body, including a human body, is suitable. Suitable examples are screw treads, which can be used to screw the electrostimulation lead in the selected tissue, such as a muscle. Alternative anchoring means are flabs (e.g. 4 parts in a cross form at the end of the electrode) that will grow into the muscle, or stitching, etc.

For stimulation of the acupuncture points of the auricle of the ear, the electrical stimulation means may be designed such as in the P-stim® device of E. Biegler GmbH (Austria). In an alternative embodiment the stimulation means are mechanical stimulation means. Mechanical stimulation is suitable for stimulating the mechanoreceptors in the dorsolateral area of the nasopharynx, the acupuncture point GV26 of the nasal philter and the acupuncture points on the auricle of the ear. Mechanical stimulation means are means that are suitable for touching with an elastic nylon fibre and thin polyvinyl catheter, or providing pressure to these parts of the subject's body. Mechanical stimulation may be also provided by means of gas pressure pulses. Other suitable means for providing mechanical pressure comprise acupuncture, acupressure, electro-acupuncture electro-acupressure (combination of mechanical and electrical stimulation).

In an alternative embodiment the stimulation means are chemical stimulation means. Chemical stimulation is suitable for stimulating the upper airways innervated by the trigeminal, olfactory and glossopharyngeal nerves. It has been found that a number of chemical stimuli induce arousal reaction and some degree of resuscitation by stimulating chemical receptors in the upper airways. These receptors are amongst others involved in olfactory sensing and provoking a short lasting increased inspiratory effort (a sniff) diverting the airflow with an odorous substance to the olfactory region of the upper airways to be detected and identified. The chemical stimulation may be induced by contacting the upper airways with a chemical composition inducing resuscitation. The chemical composition at the time of contacting with the pharynx is preferably in a gas or aerosol form. Many odors are the result of a mixture of chemical compounds.

Chemical induction of resuscitation may be provided by trigemino-olfactoric stimulants comprising for example one or more of, vanillin, amylacetate, propionic acid or phenylethylalcohol. However, it is explicitly stated that the present invention is not restricted to chemical stimulation with these odors/compounds.

For distributing the chemical composition the chemical stimulation means may comprise a spraying means. The spraying means may be suitable for spraying a (pressurized) gas and/or spraying (including nebulising) a liquid. Suitable spraying means are known to the skilled person. The spraying means is suitable for spraying a chemical composition in the vicinity of the nose and/or mouth of the subject. In this way the subject may inhale the odor composition through the nose, such that the pharyngeal mucous membrane may be chemically stimulated by the constituents of the chemical composition.

The device according to the invention in a preferred embodiment is at least partly implantable in a human body. Preferably the device is fully implantable in a human body. Implantation is especially suitable when using electrical and/or mechanical stimulation means. Complete implantation of the device will make its use easier for the subject as there will be no parts on the surface of the subject's body. An implanted device may serve as an alternative for a positive pressure supplying device preventing airway obstruction. giving the subject the same freedom as everybody else has. From cardiac pacemakers it is known that the battery life can be as long as 10 years. With the presented device the battery life can be expected to be much longer, or the device can be made much smaller, as it does not have to stimulate as often as a cardiac pacemaker. In cardiac pacemakers, approximately 70% of the pacemaker's volume is taken up by the battery and connectors.

An implantable device according to the invention may be designed such that it does not comprise any external detection or stimulation leads. Such a device may use a conductive housing as an antenna for detecting electric activity of the human body e.g. for the detection of an EEG. The conductive housing may similarly be used to guide an electric current to the part of the human body in its direct proximity. Such a device may be implanted in a part of the human body where electric stimulation may suitably be applied to obtain resuscitating stimulation of the respiratory area of the brain stem with an induction of an aspiration reflex, e.g. in the nasopharyngeal area. In a different embodiment the device according to the present invention is suitable for wearing on or behind a mammalian ear, preferably a human ear. A number of devices for wearing on the human ear are known in modern life, such as (wireless) audio headset for (mobile) phones and various music players. A further example of a device that is worn behind the ear is the P-STIM® device of E. Biegler GmbH (Austria). The skilled person will understand how to use the concepts for wearing a device comprising a battery and (micro) electronics on the human ear, as used in these headsets and the P-STIM® device, in the device according to the present invention. According to a further aspect the invention relates to a method for providing a resuscitating treatment, including reversal of life threatening functional disorders, and normalization of vital functions concerned, to a subject in need thereof. The method according to the invention comprises the steps of:

monitoring whether the subject is in need of resuscitation or elimination or alleviation of functional disorders;
providing resuscitating stimulation of the respiratory area of the subject's brain stem, preferably at a location distant from said respiratory area;
influencing secondarily the regulatory mechanisms of other vital functions supporting their normalization.

Monitoring of the subject may be in various ways known to the skilled person. A number of possible ways for monitoring the subject's need for resuscitation have already been discussed in the above.

Preferred embodiments of the method of the invention relate to the way of stimulation of the respiratory area of the subject's brain stem. Stimulation is preferably at (or is better from) a location distant from the subject's respiratory area. Suitable locations for resuscitating stimulation according to the invention are the pharynx, preferably the oropharynx, more preferably the nasopharynx, most preferably the nasopharyngeal area around the tuba auditiva.

Alternatively resuscitating stimulation may be provided by stimulation of the nasal philter, preferably stimulation of acupuncture point GV26.

In a further alternative embodiment of the invention resuscitating stimulation is provided by stimulation of the acupuncture points on the auricle of the ear.

The resuscitating or normalizing stimulation may be provided with any means suitable for providing resuscitating stimulation of the respiratory center of the human brain stem. According to preferred embodiments of the method according to the invention use is made of electrical stimulation, mechanical stimulation or chemical stimulation. Use of electrical stimulation is most preferred. Suitable means for providing resuscitating stimulation have been discussed in the above.

The method according to the invention is suitable for the treatment of one or more of but not limited to apnoea, such as central apnoea or obstructive apnoea, transient ischemic attacks (TIA), hypotension, syncope, haemorrhagic shock (loss of blood), bronchospasm, laryngospasm, hiccup, tremor associated with Parkinson's disease, epileptic seizure, absence type epilepsy, migraine, alternating hemiplegia, Alzheimers disease, depression, anorexia nervosa, bulimia, autism, psychiatric disorders, insomnia, sleep paralysis, comatose states. As used in this specification the term treatment should be construed to encompass alleviation of discomfort or provide reversal of life threatening functional disorders.

BRIEF DESCRIPTION OF THE FIGURES

The present invention will now be further illustrated with reference to the following examples and the annexed figures wherein:

FIG. 1 is a schematic cross section of a part of the human head and neck;

FIG. 2 is a detail from FIG. 1;

SUMMARY OF THE INVENTION

Figure 3A:
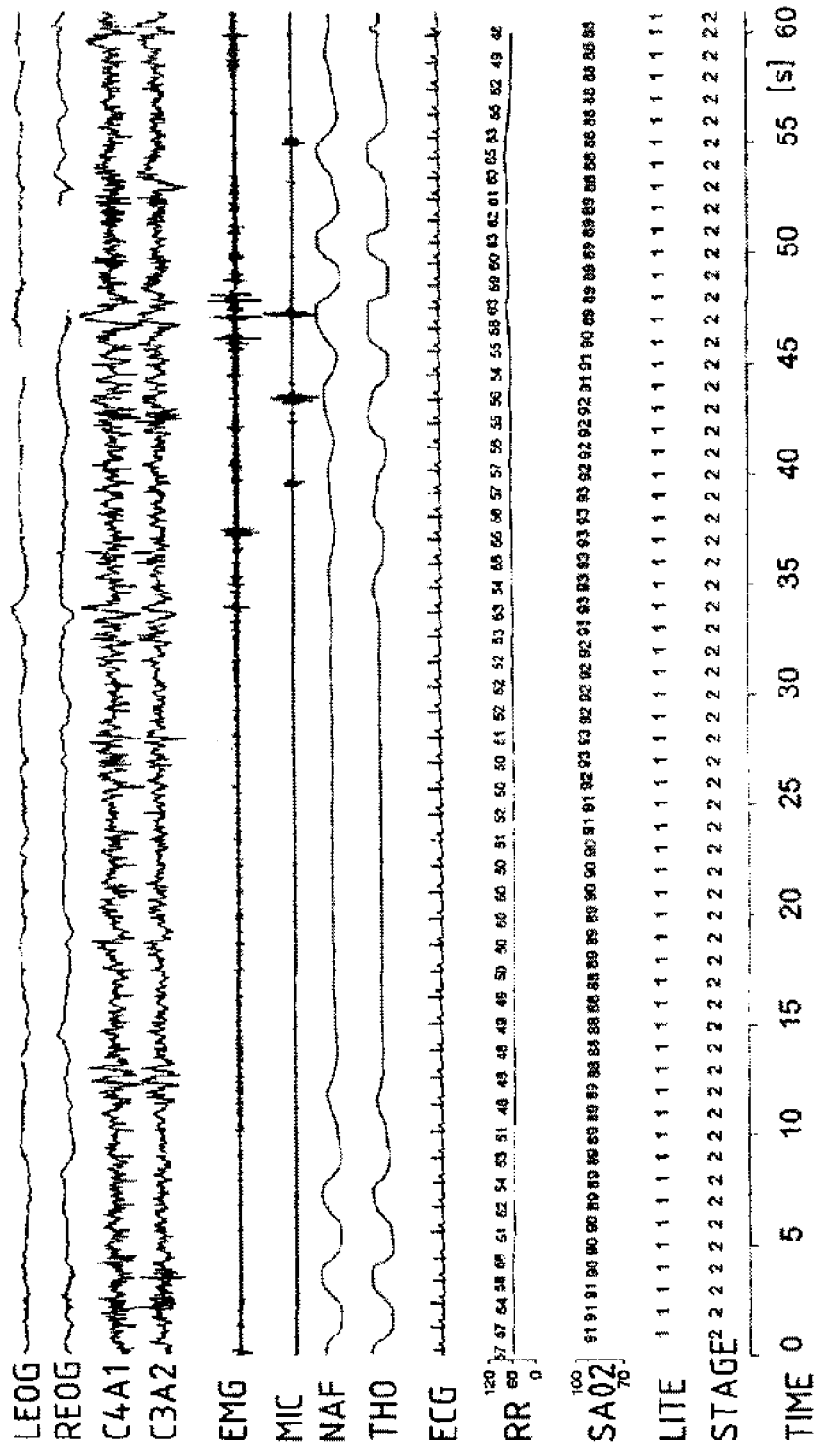
FIG. 3A is a graph of polysomnographic data of a first adult human individual suffering from sleep apnoea with central sleep apnoea accompanied by bradycardia.

As shown in FIG. 1 the pharynx is situated from the underside of the skull to the level of cervical vertebra C6. The pharynx may be divided in three compartments, the nasopharynx (roughly situated behind the nasal cavity between arrows 1 and 2), the oropharynx (roughly situated behind the oral cavity between arrows 2 and 3) and the laryngopharynx (roughly situated behind the larynx between arrows 3 and 4).

FIG. 2 shows the preferred location of resuscitating stimulation of the pharynx. Resuscitating stimulation is preferably administered in the area of the nasopharynx enclosed by reference marks A, B, C, D surrounding the tuba auditiva 5. More preferably resuscitating stimulation is administered in the direct proximity of the tuba auditiva 5 indicated by the hatched lines in FIG. 2.

DETAILED DESCRIPTION OF THE INVENTION

Experimental Example 1

Patient J. M, 55 years old male with moderate sleep apnoea of mixed type (RDI (Respiratory Disturbance Index)=35/h) and excessive daytime sleepiness (ESS (Epword Sleepiness Scale) score 15 from 24) was examined (whole-night polysomnography and testing of the optimal value of continuous positive airway pressure therapy—CPAP) with continuous recording of parameters as follows:

LEOG and REOG—left and right electro-oculogram (eye bulb movements)

C4A1 and C3A2—electroencephalogram—EEG (brain action potentials)

EMG—electromyogram—action potentials of muscles

MICRO—microphone recording of respiratory sounds (snoring)

NAF—nasal airflow recorded by thermistor

THO—thoracic movements by tensometer

ECG—electrocardiogram, 2. lead

RR—heart rate from ECG [Min-1].

SAO2—oxygen saturation in the arterial blood [%]

LITE—intensity of ambient light [%]

Time—time course in the experiment

STAGE—Non-REM sleep stage 2: S2

Figure 3B:
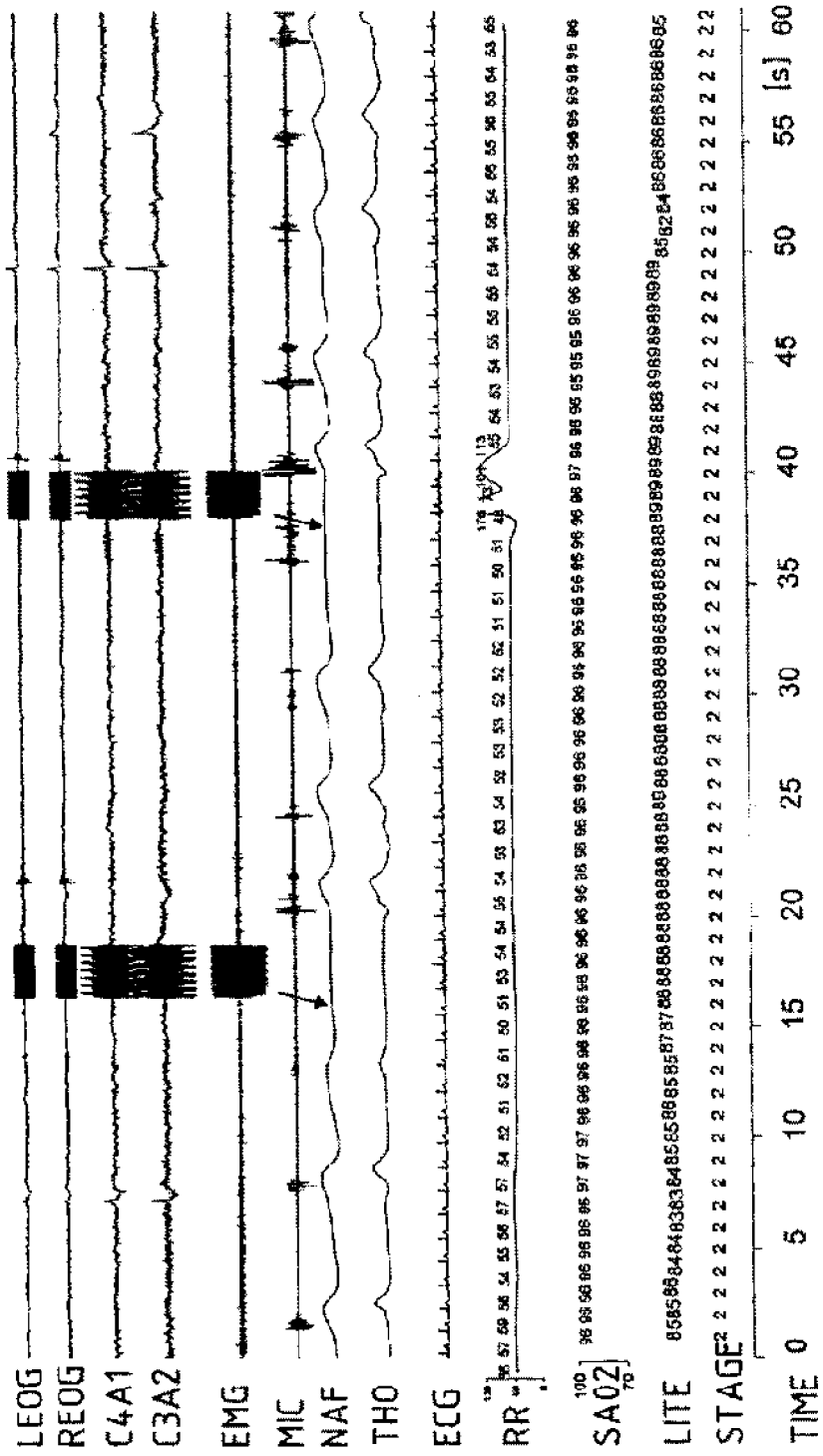
FIG. 3B is a graph of polysomnographic data of the first adult human individual suffering from sleep apnoea with non-REM sleep development of 2 short episodes of central sleep apnoea lasting 8 and 9 seconds interrupted by electro-acustimulation of point GV.

The results of this experiment are shown in FIGS. 3A-3B and discussed below.

FIG. 3A. Central sleep apnoea (stop of both the thoracic movements and airflow) lasting approximately 23 sec, accompanied by bradycardia (decrease in heart rate from 51-53/min to 48-50/min and decrease in O2 saturation from 93% to 88% with a delay of about 15 seconds). Later there was a gradual renewal of spontaneous breathing with snoring, hyperventilation and tachycardia (65/min).

FIG. 3B. In Stage 2 Non-REM sleep development of 2 short episodes of central sleep apnoea lasting 8 and 9 sec were interrupted by electro-acustimulation of point GV26, provoking prompt thoracic movement and inspiratory airflow with short sniff-like sound, followed by spontaneous breathing without hyperventilation, snoring and marked changes in heart rate and O2 saturation. It should be noted that the values for ECG and RR from about 37 s to 40 s do not correspond to the physiological value of the subject. Instead in this interval ECG and RR measurement is disturbed by the electro stimulation. Reflex activation of the brainstem inspiratory neurons via acupuncture point GV26 was adequate for the reversal of central sleep apnoea.

Experimental Example 2

Patient Z. S, 51 years old male with severe sleep apnoea of mixed type (RDI=48/h) was examined (whole-night polysomnography) with continuous recording of parameters as follows:

LEOG and REOG—left and right electro-oculogram (eye bulb movements)

C4A1 and C3A2—electroencephalogram—EEG (brain action potentials)

EMG—electromyogram—action potentials of muscles
MICRO—microphone recording of respiratory sounds (snoring)
NAF—nasal airflow recorded by thermistor
THO—thoracic movements by tensometer
ECG—electrocardiogram, 2. lead
RR—heart rate from ECG [Min-1].
SAO2—oxygen saturation in the arterial blood [%]
LITE—intensity of ambient light [%]
Time—time course in experiment
STAGE—Non-REM sleep stage 1: S1; stage 2: S2

Figure 4A:
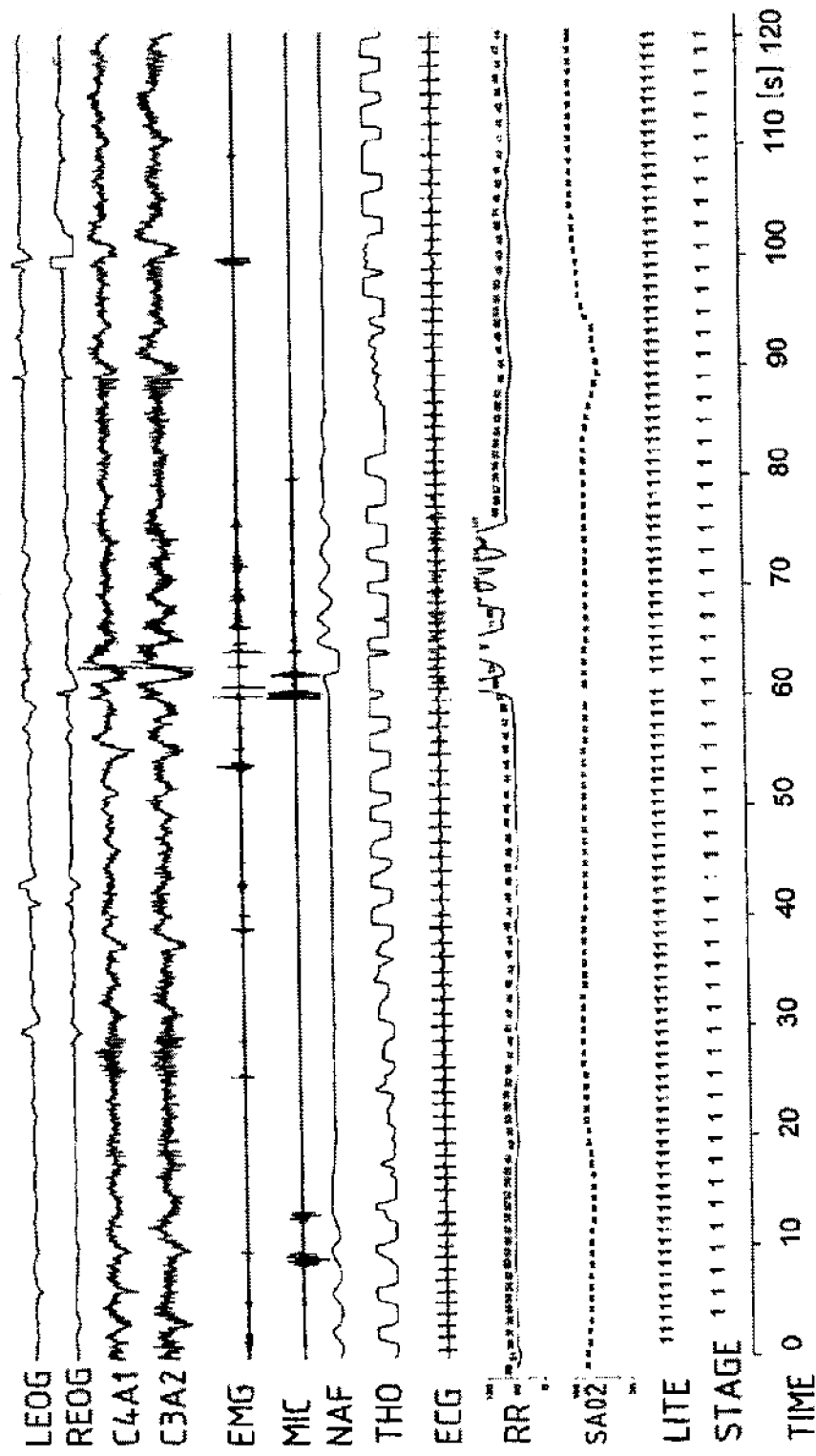
FIG. 4A is a graph of polysomnographic data of a second adult human individual suffering from sleep apnoea with obstructive sleep apnoea accompanied by bradycardia.
Figure 4B:
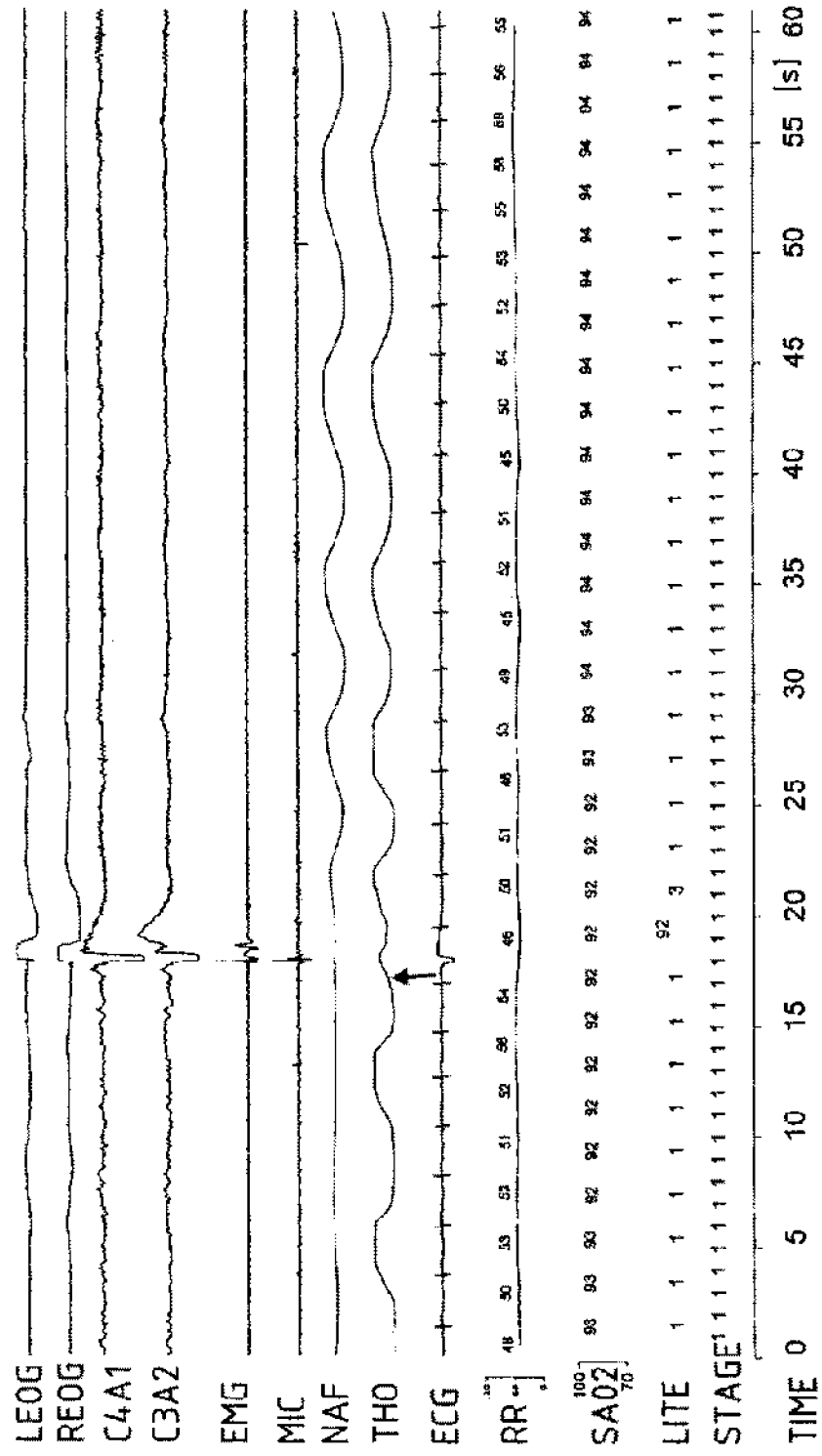
FIG. 4B is a graph of polysomnographic data of the second adult human individual suffering from sleep apnoea with non-REM sleep developing episode of obstructive sleep apnoea after 10 seconds of duration interrupted by gentle mechanical contacts of the nasopharyngeal mucosa with a flexible nylon fiber.

The results of this experiment are shown in FIGS. 4A-4B and discussed below.

FIG. 4A. Obstructive sleep apnoea (stop of both the thoracic movements and airflow in spite of strong persisting thoracic movement) lasting approximately 46 sec, accompanied by bradycardia (decrease in heart rate from 53/min to 44/min and decrease in O2 saturation from 93% to 81% with some delay). Later there was a gradual renewal of spontaneous breathing with snoring, hyperventilation and tachycardia increase in heartrate (70/min). It should be noted that the values for ECG, RR, C4A1 and C3A2 from about 60 s to 78 s do not correspond to the physiological value for the subject. Instead in this interval ECG, RR, C4A1 and C3A2 measurement is disturbed by excessive thoracic movement and a strong EMG.

FIG. 4B. In Stage 1 Non-REM sleep a developing episode of obstructive sleep apnoea after 10 sec of duration was interrupted by gentle mechanical contacts of the nasopharyngeal mucosa with a flexible nylon fiber, provoking prompt thoracic movement and inspiratory airflow with short sniff-like sound, followed by spontaneous breathing without marked changes in heart rate and O2 saturation. Reflex activation of the brainstem inspiratory neurons with contact stimulation of the nasopharynx was adequate for the reversal of obstructive apnoea.

Experimental Example 3

Patient M. H, 56 years old male with moderate sleep apnoea of central type (RDI=32/h) was examined (whole-night polysomnography) with continuous recording of parameters as follows:
LEOG and REOG—left and right electro-oculogram (eye bulb movements)
C4A1 and C3A2—electroencephalogram—EEG (brain action potentials)
EMG—electromyogram—action potentials of muscles
MICRO—microphone recording of respiratory sounds (snoring)
NAF—nasal airflow recorded by thermistor
THO—thoracic movements by tensometer
ECG—electrocardiogram
RR—heart rate from ECG [Min-1] are not indicated for technical reasons
SAO2—oxygen saturation in the arterial blood [%]
LITE—intensity of ambient light [%]
Time—time course in experiment
STAGE—Non-REM sleep stage 1: S1; stage 2: S2

Figure 5A:
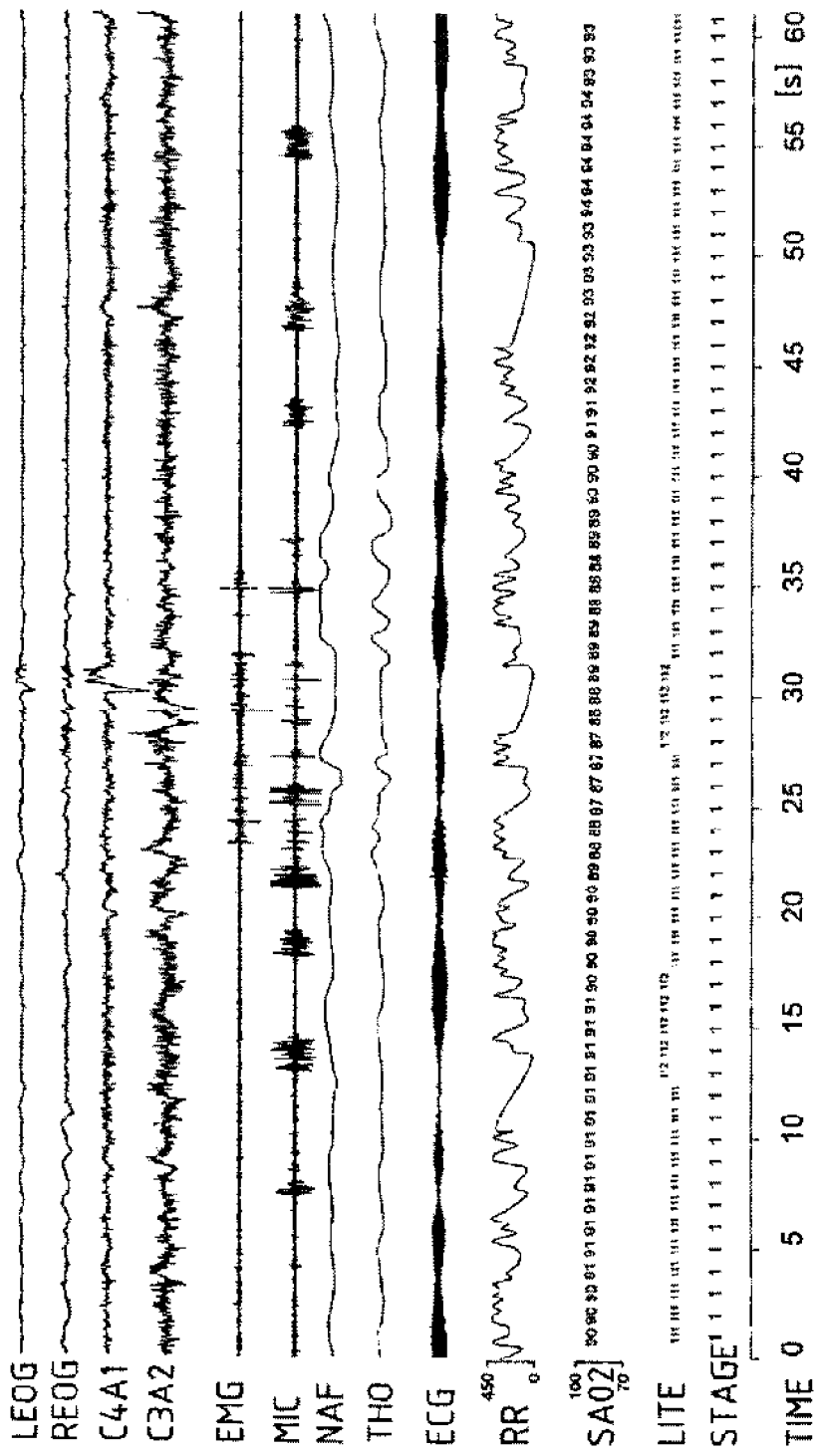
FIG. 5A is a graph of polysomnographic data of a third adult human individual suffering from sleep apnoea with a non-REM sleep stage of period of hyperapnoea lasting approximately 25 seconds; preceded and followed by two episodes of hypopnoea suggesting a non-stable sleep in a supine position.
Figure 5B:
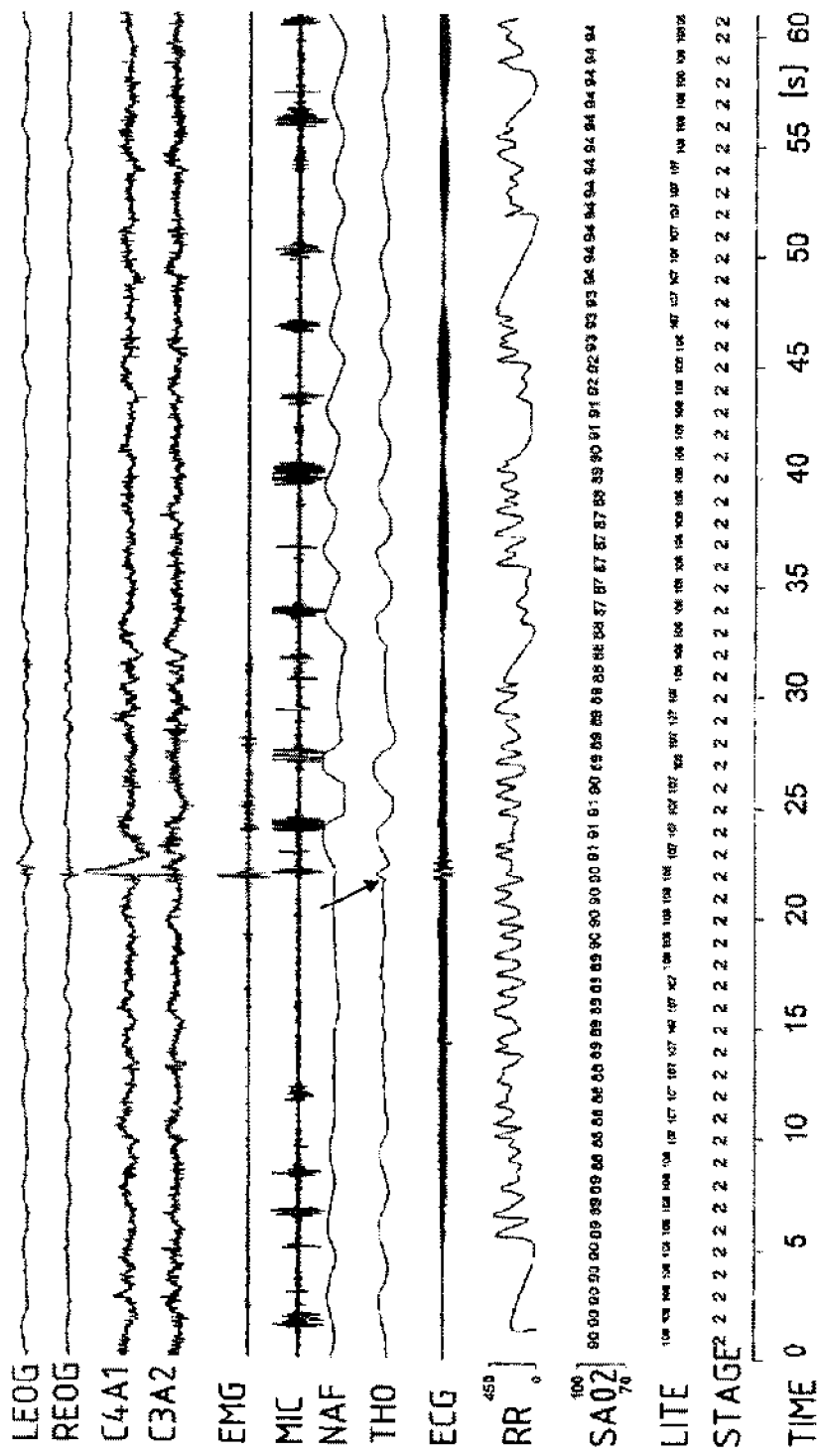
FIG. 5B is a graph of polysomnographic data of the third adult human individual suffering from sleep apnoea with non-REM sleep developing an episode of central sleep apnoea interrupted by gentle mechanical contacts of the nasopharyngeal mucosa with a flexible nylon fiber.

The results of this experiment are shown in FIGS. 5A-5B and discussed below.

FIG. 5A. In a Non-REM sleep stage 1 a period of hyperpnoea lasting approximately 25 sec (in the middle of the figure) is preceded and followed by two episodes of hypopnoea suggesting a non-stable sleep in a supine position. Alteration of breathing pattern is reflected by periodic changes in arterial O2 saturation between 91%, 87% and 94% with a delay of 15-20 sec. Records of ECG and heart rate (RR) in FIGS. 5A and 5B do not represent the actual physiological values for the subject due to technical problems.

FIG. 5B. In Stage 2 Non-REM sleep a developing episode of central sleep apnoea after 8 sec of duration was interrupted by gentle mechanical contacts of the nasopharyngeal mucosa with a flexible nylon fiber (indicated by an arrow), provoking prompt thoracic movement and inspiratory airflow with short sniff-like sound. This was followed by spontaneous breathing without marked changes in O2 saturation (from 90% through 88% to 91%). Reflex activation of the brainstem inspiratory neurons with contact stimulation of the nasopharynx was adequate for the reversal of an episode of central sleep apnoea.

The presented results demonstrate that both electroacupressure of point GV 26 (FIGS. 3A-3B) and gentle mechanical stimulation of the nasopharyngeal mucosa (FIGS. 4A-4B and FIGS. 5A-5B) can interrupt episodes of central and obstructive sleep apnoea prevent development of marked changes in heart rate and O2 saturation and restart of spontaneous breathing in adult human individuals.

Example 1

An implantable device comprises a stainless steel or titanium casing. Enclosed in the casing is a battery (lithium iodine with nanocrystalline cathode components, as generally used in cardiac pacemakers), and the microelectronics. The microelectronics comprises a system for recording an electromyogram (EMG) detected by a detection electrode connected to the device. The detection electrode is suitable for attachment to the diaphragm. The EMG data (intensity, frequency, repeatability of phasic activity), is processed in a microprocessor. The microprocessor is designed to activate a wave function generator if the EMG does not satisfy a predetermined criterion, such as a lack of normal EMG activity for >10 sec (central apnoea) or extremely strong EMG activity accompanied by stop of airflow (obstructive apnoea). Upon activation the wave function generator generates a predetermined wave, such as a sinus wave, block wave, spike train or any combination in a suitable frequency, duration and amplitude that is guided through the electrical wires of an electric stimulation lead to its stimulation electrode. The electrostimulation lead is suitable to be anchored in the dorsolateral area of the nasopharynx.

Example 2

Another device of the invention is based on the stimulation of the upper airways by chemical stimulation. The electronic device may be attached near the head of the sleeping subject. The device monitors the breathing of the patient by monitoring sound with the use of a microphone, or alternatively the airflow with a flowmeter. Upon an episode of apnoea, the device by means of spraying from a reservoir will release a chemical composition suitable for stimulating the mucous membrane of the upper airways. This will induce sniffing and resuscitation in the subject. Resuscitation will normalize breathing, blood pressure and heart rate. The chemical composition in the reservoir can be replaced. This facilitates refilling and makes it possible to replace the chemical composition with other compositions. Replacement with a differing chemical composition prevents loss of response due to adaptation. The device can also comprise several reservoirs with different chemicals enabling randomisation. A device like this can also be used to help prevent sudden infant death (SID). The advantage of this method is that there is no treatment, if there is no apnoeic episode.

Example 3

There are also other ways to reactivate the failing brainstem centers controlling the vital functions and cause resuscitation. One example is the electrical or mechanical stimulation of the acupuncture point GV26 of the nasal philter. This could be provided by an apparatus, attached under the patients nose, to monitor breathing by detecting airflow by a flowmeter and to stimulate the acupuncture point GV26 under the nose during an apnoeic episode.

Example 4

Another example is the stimulation of acupuncture points on the auricle of the ear. It is difficult to locate these points exactly, but once located stimulation of these points may result in similar reflex effects as stimulation of the nasopharynx or nasal filter. An electronic "ear cap" monitoring the breathing of the patient, for example by respiratory sound, and providing stimulation during apnoeic episodes would help the patients.

It should be understood that the embodiments presented in the examples above are solely intended to illustrate the present invention and are not intended to limit the scope of the invention.

The invention claimed is:

1. A method for providing a resuscitating treatment of a human being, comprising:
   sensing at least one of human muscle activity, human breathing activity, human neural activity and human cerebral activity,
   determining whether said human being is in a state of developing apnoea by at least one processing unit based on said sensing,
   provoking an induced aspiration reflex by a resuscitating stimulation of a respiratory area of a human brain stem by providing a stimulus with a stimulation device to a location distant from said respiratory area of the human brain stem upon said at least one processing unit determining said state of developing apnoea, said location being one of a nasal filter of the human being and a nasopharyngeal area of the human being.

2. The method according to claim 1, wherein said provoking said induced aspiration reflex by said resuscitating stimulation of the respiratory area of the human brain stem includes providing said stimulus to acupuncture point GV26 on said human nasal filter.

3. The method according to claim 1, wherein said sensing includes sensing at least one of a gas flow, gas composition, gas pressure, gas temperature, body temperature and sound.

4. The method according to claim 1, wherein said stimulation is provided by at least one of an electrical response device, a device for spraying a chemical composition and a mechanical response device.

5. The method according to claim 1, wherein said stimulation device comprises an elastic nylon fiber and thin polyvinyl catheter.

6. The method according to claim 1, wherein said stimulation device comprises a unit for providing gas pressure pulses if it has to provide a stimulus to said nasopharyngeal area.

7. The method according to claim 1, wherein said stimulation device comprises a unit for providing at least one of gas pressure pulses, acupuncture, acupressure, electro-acupuncture, and electro-acupressure if it has to provide a stimulus to the nasal filter.

8. The method according to claim 1, wherein said stimulation device comprises electrodes arranged to be placed on a human skin.

9. A resuscitation device for humans comprising:
   a sensor configured to detect a number of parameter values in a human being;
   at least one memory configured to store a predetermined function;
   at least one processing unit connected to the sensor and the memory and configured to process the number of detected parameter values in said predetermined function to determine whether said human being is in a state of developing apnoea;
   a response device connected to the processing unit and configured to provide a response as a function of the number of processed parameter values by the at least one processing unit when said at least one processing unit has determined that said human being is in said state of developing apnoea;
   wherein said resuscitation device is an apparatus comprising both said sensor, said memory, said at least one processing unit and said response device, said apparatus being configured to be attached under a human's nose, said sensor being configured to sense breathing activity, and said response device comprising a stimulation device configured to provoke an induced aspiration reflex by a resuscitating stimulation of the respiratory area of the human brain stem by providing a stimulus to one of a nasal filter of the human being and a nasopharyngeal area of the human being.

10. The resuscitation device according to claim 9, wherein said apparatus is configured to provoke said induced aspiration reflex by said resuscitating stimulation of the respiratory area of the human brain stem by providing said stimulus to acupuncture point GV26 on said human nasal filter.

11. The resuscitation device according to claim 9, wherein said sensor is configured to sense at least one of a gas flow, gas composition, gas pressure, gas temperature, body temperature and sound.

12. The resuscitation device according to claim 9, wherein the response device is at least one of an electrical response device, a device for spraying a chemical composition and a mechanical response device.

13. The resuscitation device according to claim 9, wherein said stimulation device comprises an elastic nylon fiber and thin polyvinyl catheter.

14. The resuscitation device according to claim 9, wherein said stimulation device comprises a unit for providing gas pressure pulses if it has to provide a stimulus to said nasopharyngeal area.

15. The resuscitation device according to claim 9, wherein said stimulation device comprises a unit for providing at least one of gas pressure pulses, acupuncture, acupressure, electro-acupuncture, and electro-acupressure if it has to provide a stimulus to the nasal filter.

16. The resuscitation device according to claim 9, wherein said stimulation device comprises electrodes arranged to be placed on a human skin.

* * * * *